(12) United States Patent
Pedicini et al.

(10) Patent No.: US 12,090,620 B2
(45) Date of Patent: Sep. 17, 2024

(54) ROTARY TOOL WITH REDUCED REACTIONARY TORQUE

(71) Applicant: CSP Consulting, LLC, Brentwood, TN (US)

(72) Inventors: Christopher Pedicini, Brentwood, TN (US); Joshua Pedicini, Nashville, TN (US)

(73) Assignee: CSP CONSULTING, LLC, Brentwood, TN (US)

(*) Notice: Subject to any disclaimer, the term of this patent is extended or adjusted under 35 U.S.C. 154(b) by 0 days.

(21) Appl. No.: 18/531,774

(22) Filed: Dec. 7, 2023

(65) Prior Publication Data

US 2024/0189975 A1 Jun. 13, 2024

Related U.S. Application Data

(60) Provisional application No. 63/459,815, filed on Apr. 17, 2023, provisional application No. 63/447,199, filed on Feb. 21, 2023, provisional application No. 63/439,681, filed on Jan. 18, 2023, provisional application No. 63/431,192, filed on Dec. 8, 2022.

(51) Int. Cl.
*B25F 5/00* (2006.01)

(52) U.S. Cl.
CPC .................... *B25F 5/001* (2013.01)

(58) Field of Classification Search
CPC ........................................................ B25F 5/001
USPC ............................................................ 173/1
See application file for complete search history.

(56) References Cited

U.S. PATENT DOCUMENTS

| | | | | |
|---|---|---|---|---|
| RE45,112 E | * | 9/2014 | Zhang | B23D 59/001 |
| | | | | 173/4 |
| 2004/0211573 A1 | * | 10/2004 | Carrier | B25F 5/00 |
| | | | | 173/183 |
| 2006/0081386 A1 | * | 4/2006 | Zhang | B25B 21/00 |
| | | | | 173/2 |
| 2008/0011102 A1 | * | 1/2008 | Schell | B25F 5/001 |
| | | | | 73/862.22 |
| 2008/0099217 A1 | * | 5/2008 | Seith | B25B 21/026 |
| | | | | 173/1 |

* cited by examiner

*Primary Examiner* — Praachi M Pathak
(74) *Attorney, Agent, or Firm* — XSENSUS LLP

(57) ABSTRACT

A rotary tool may include a motor, a first clutch, a first drive path, a second drive path, a second clutch, a rotating mass, and an output anvil. The rotary tool may drive, by the motor and the first clutch, a first drive path that causes the output anvil to rotate at a speed. The rotary tool may selectively enable, by the motor and the second clutch, a second drive path that causes the rotating mass to engage to the output anvil and increase a torque delivered to the output anvil.

18 Claims, 14 Drawing Sheets

ROTARY TOOL WITH REDUCED REACTIONARY TORQUE

CROSS-REFERENCE TO RELATED APPLICATION

This application claims the benefit of U.S. Provisional Application No. 63/431,192, filed Dec. 8, 2022, U.S. Provisional Application No. 63/439,681, filed Jan. 18, 2023, U.S. Provisional Application No. 63/447,199, filed Feb. 21, 2023, and U.S. Provisional Application No. 63/459,815, filed Apr. 17, 2023, each of which is incorporated herein by reference in its entirety.

BACKGROUND

Rotary tools are used in various applications, such as woodworking, metalworking, construction, and/or automotive repair. The rotary tools rotate various attachments or bits, providing precision and control for a multitude of tasks.

SUMMARY

Some implementations described herein relate to a rotary tool with increases torque. The rotary tool may include a motor; a drive shaft operatively coupled to the motor; an output anvil operatively coupled to the drive shaft; a rotating mass; and a clutch operatively coupled to the rotating mass and the output anvil, wherein the clutch engages the rotating mass to the output anvil when a speed of the output anvil drops to less than a design speed, and wherein after such engagement the clutch disengages the rotating mass from the output anvil to allow the rotating mass to reaccelerate.

Some implementations described herein relate to a method for operating a rotary tool, the rotary tool including a motor, a first clutch, a first drive path, a second drive path, a second clutch, a rotating mass, and an output anvil, the method comprising: driving, by the motor and the first clutch, a first drive path that causes the output anvil to rotate at a speed; and selectively enabling, by the motor and the second clutch, a second drive path that causes the rotating mass to engage to the output anvil and increase a torque delivered to the output anvil.

Some implementations described herein relate to a rotary tool including a motor; a controller; a drive shaft operatively coupled to the motor; an output anvil operatively coupled to the drive shaft; a flywheel; and a clutch operatively coupled to the flywheel and the output anvil, wherein the clutch engages the flywheel to the output anvil, wherein the motor power is reduced by the controller during engagement of the clutch, and wherein after the clutch has been engaged for a period of time, the clutch disengages the flywheel from the output anvil and the motor power is increased to reaccelerate the flywheel.

DETAILED DESCRIPTION OF EXAMPLE EMBODIMENTS

Figure 1:
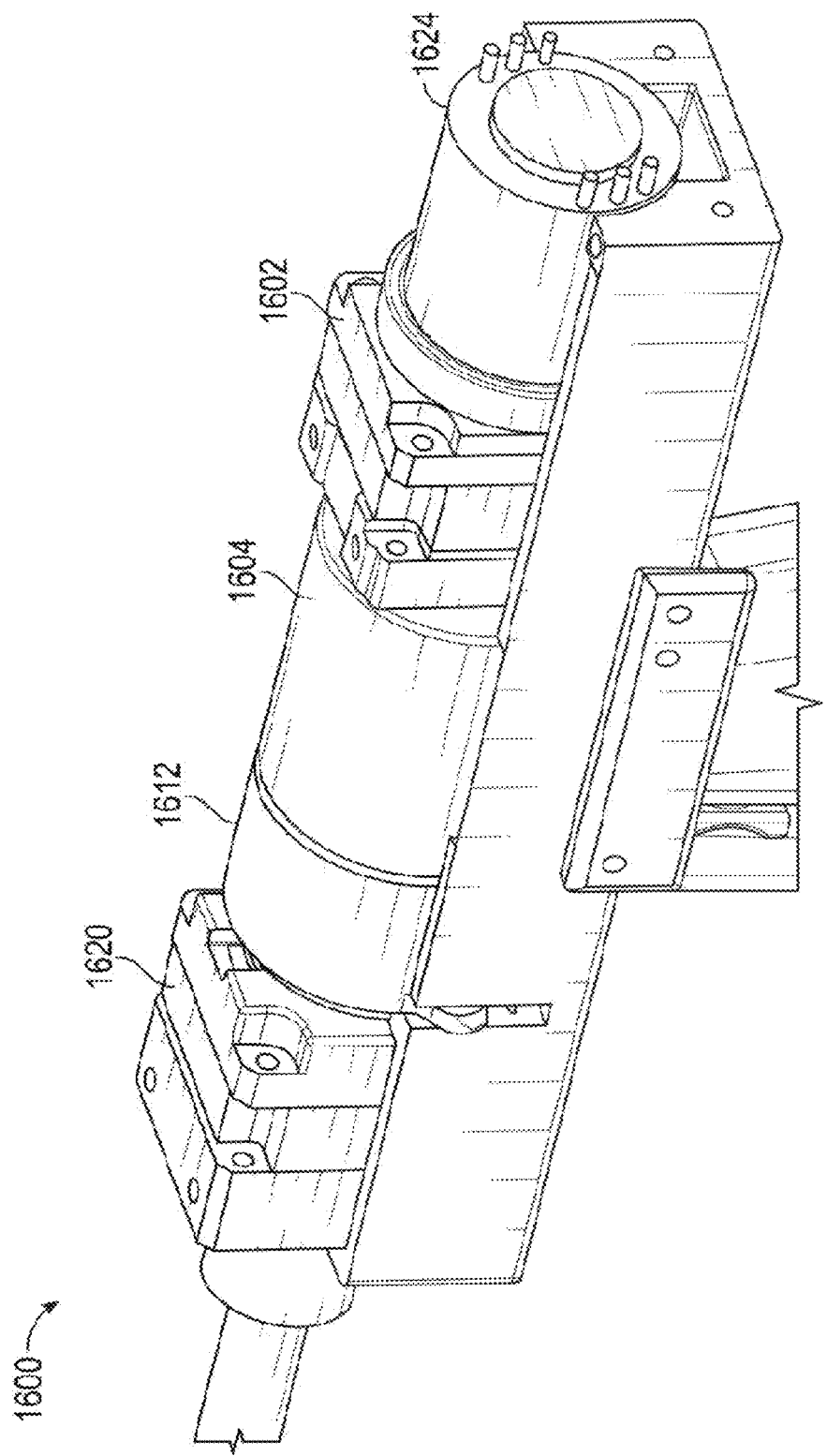
FIG. 1 is a diagram of an example rotary tool with reduced reactionary torque.

The following detailed description of example implementations refers to the accompanying drawings. The same reference numbers in different drawings may identify the same or similar elements.

A rotary tool (e.g., a drill, among other examples) can be used (e.g., by an operator, a worker, and/or a robot, among other examples) to perform one or more operations. For example, the rotary tool may be used for cutting, engraving, polishing, sanding, grinding, and drilling operations. To perform the one or more operations, the operator may cause a component (e.g., an attachment or bit, among other examples) of the rotary tool to rotate and interact with a workpiece. As an example, the rotary tool may include a motor to provide a rotational force that causes the component to rotate. As the component rotates, the operator causes the component to interact with the workpiece, and the rotational motion, combined with the component, creates an action based on the attachment or the bit.

However, during the one or more operations, the interaction between the component and the workpiece generates a reactionary torque (e.g., a reactionary force that opposes rotation of the component). In some cases, a high reactionary torque may be generated which requires the operator of the rotary tool to exert a high counteracting force from his wrist to overcome the high reactionary torque and maintain control over movement associated with the rotary tool. If the operator has to overcome high reactionary torque during the one or more operations, this introduces drawbacks and challenges which include, but are not limited to, operator fatigue, wrist injury, and reduced precision. Furthermore, existing techniques employed to mitigate high reactionary torque during the one or more operations generate excessive noise levels, which can lead to hearing damage of the operator.

Some implementations described herein relate to a rotary tool with reduced reactionary torque. For example, the rotary tool may include a motor, a drive shaft operatively coupled to the motor, an output anvil operatively coupled to the drive shaft, a rotating mass (e.g., a flywheel), a clutch operatively coupled to the rotating mass, and a controller. In some implementations, the controller may measure the rotational speed of the output anvil and based on comparison of that speed to a desired speed use a clutch to selectively couple the rotating mass to the output anvil to transmit additional torque from the rotating mass to the output anvil. As an example, if the controller determines that the output rotational speed of the output anvil drops below a threshold rotational speed, then the controller may cause the clutch to selectively couple the rotating mass to the output anvil to transmit additional torque from the rotating mass to the output anvil.

In this way, the rotary tool may selectively couple a rotating mass to the output anvil to provide a torque that overcomes a high load torque at the output anvil (e.g., via a clutch that can be mechanically and/or electronically controlled to selectively couple a rotating mass to the output anvil, as described in more detail elsewhere herein.

Figure 2:
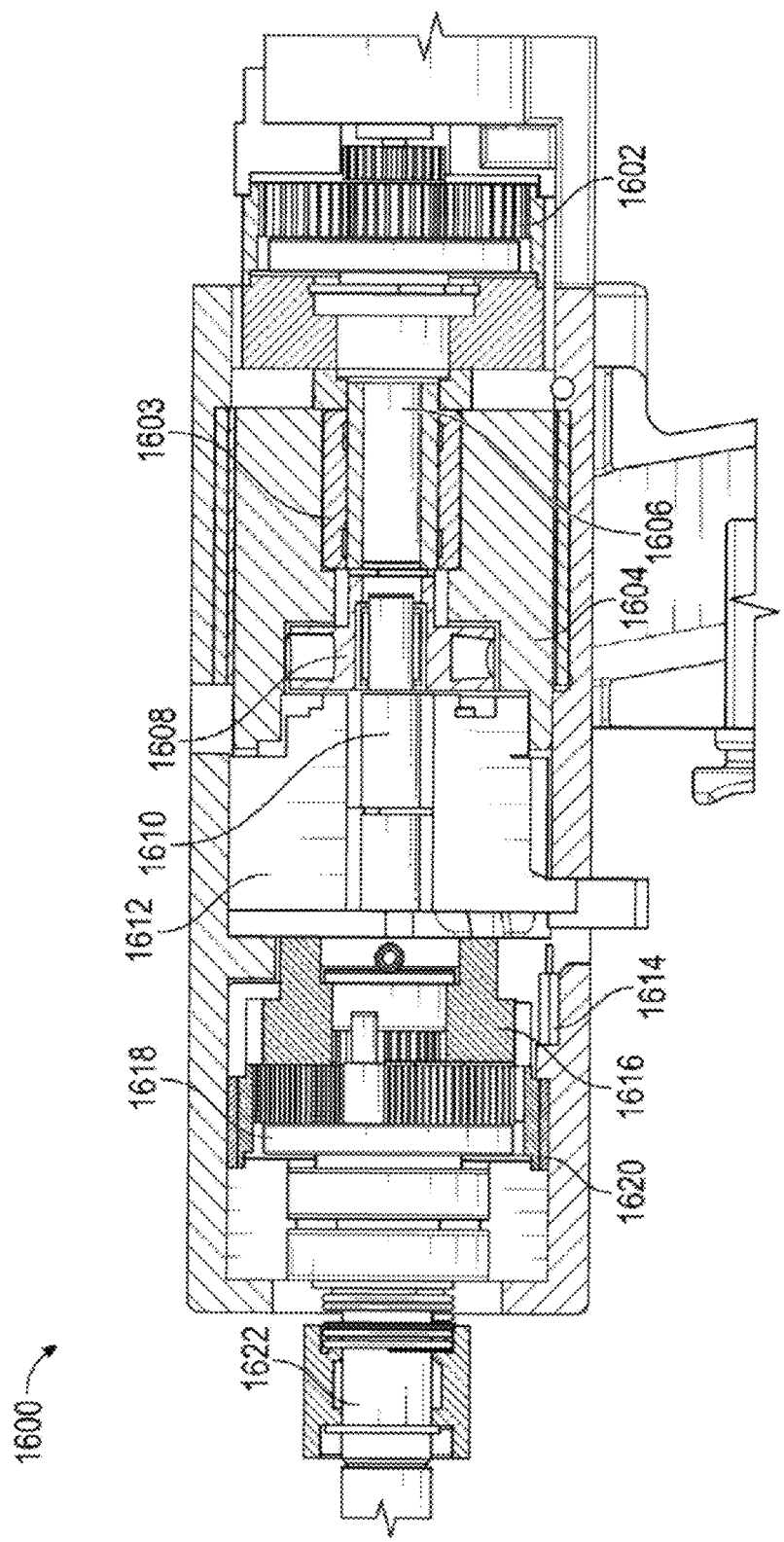
FIG. 2 is a diagrammatical cross-section of the rotary tool of FIG. 1.

FIG. 1 is a diagram of an example rotary tool 1600 with reduced reactionary torque. FIG. 2 is a diagrammatical cross-section of the rotary tool 1600 of FIG. 1. As shown in FIGS. 1-2, the rotary tool 1600 includes a primary gear box 1602, a one-way drive bearing 1603, a rotating mass 1604, a drive shaft 1606, a slip clutch 1608, a bypass shaft 1610, an electronic clutch 1612 (e.g., a wrap spring clutch, among other examples), a rotational speed sensor 1614 a carriage plate driver 1616, a gear carrier 1618, a drive path juncture 1620, and an output anvil 1622. The drive path juncture 1620 is a juncture point between two or more drive paths. The drive path juncture 1620 can be, for example, a gearbox which gearbox couples the bypass shaft 1610 through the gear carrier 1618 (or a gear ratio).

Figure 3:
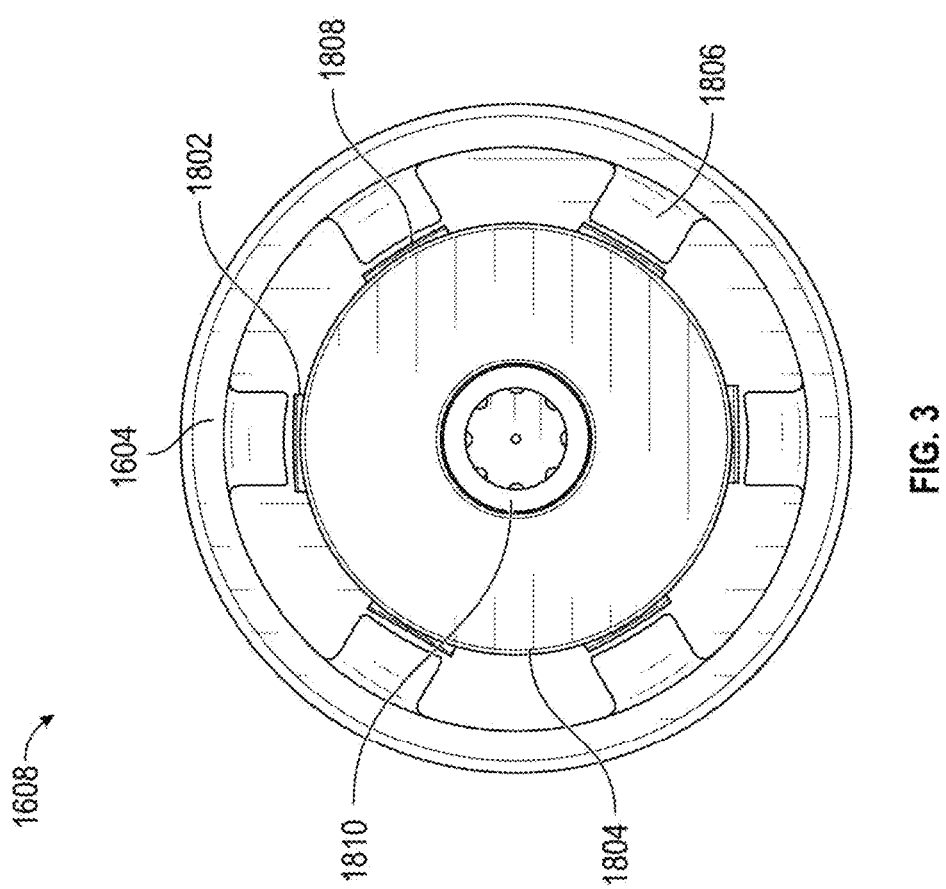
FIG. 3 is a diagram of an example magnetic slip clutch of the rotary tool of FIG. 1.
Figure 4:
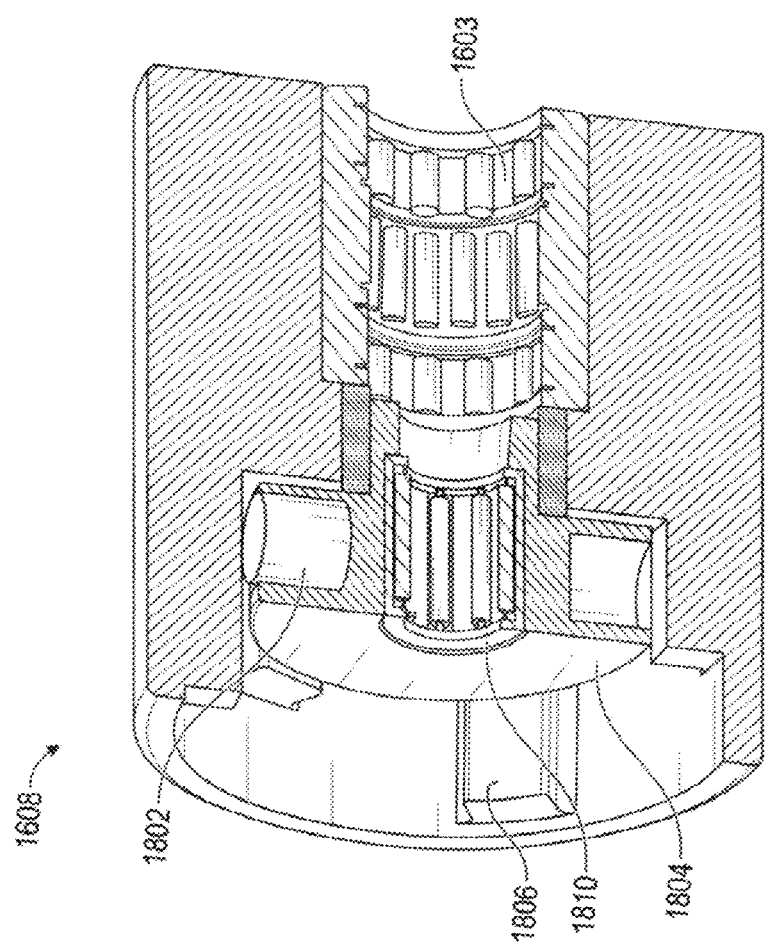
FIG. 4 is a partial diagrammatical cross-section of the magnetic slip clutch of FIG. 3 operatively coupled to an example one-way bearing.

FIG. 3 is a diagram of a magnetic slip clutch 1608 of the rotary tool 1600 of FIG. 1. FIG. 4 is a partial diagrammatical cross-section of the magnetic slip clutch 1608 operatively coupled to the one-way bearing 1603. As shown in FIGS. 3-4, the rotary tool 1600 includes magnets 1802, a center drive 1804, splined teeth 1806, an airgap 1808 (e.g., that is positioned between the magnets 1802 and the splined teeth 1806 as shown in FIG. 3), and a bypass shaft overrunning bearing 1810. The bypass shaft overrunning bearing 1810 is used to drive a bypass shaft (such as the bypass shaft 1610 shown in FIG. 2). The bypass shaft is a unique invention that enables the output anvil to be turned at a desired output rpm range (e.g., a design speed) and yet allow slippage at a design torque and as a result of said slippage to allow for operative coupling of additional torque to the output by using an alternate and parallel path. As an example, a design speed is a speed of the output anvil when the rotary tool operates with a threshold torque below the slip torque of the first drive path. As another example, a design speed may correspond to a depth of a trigger pull that controls the speed of the rotary tool. As an example, if the depth of the trigger pull is a maximum depth, then the design speed may be 3000 rpm, and if the depth of the trigger pull is an intermediate depth, then the design speed may be 1500 rpm.

As further shown in FIG. 3, the magnetic slip clutch 1608 is disposed within the rotating mass 1604. Although the rotary tool 1600 is shown and described as having the magnetic slip clutch 1608 disposed within the rotating mass 1604, the rotary tool 1600 may utilize any suitable slip or overload clutch, disposed in any suitable position associated with the rotary tool 1600.

Although the rotary tool 1600 is described as using the magnetic slip clutch 1608, the rotary tool 1600 may use any suitable clutch, such as a friction clutch, hysteresis clutch, an eddy current clutch, and/or a spring ball relief clutch, among other examples. Different clutches are associated with different breakaway or slippage characteristics. One important distinction associated with this disclosure is that the bypass shaft rotational energy is operatively communicated from the motor to the output anvil through a slip or breakaway clutch in which the torque transmitted to the operator is reduced or held steady when the torque reaches a slip torque (e.g., when the torque satisfies a torque threshold). In some implementations, the slippage or breakaway effect could be achieved by controlling or modulating an electrically activated clutch.

Accordingly, the "slip torque" of a clutch is associated with a maximum transmissible torque that may be transmitted before an angular rotation at an input side of the clutch exceeds (e.g., for a period of time) an angular rotation on an output side of the clutch.

In some implementations, an overload torque level (e.g., a torque level at the slip torque) may be approximately 25 inch-pounds (e.g., as measured by a torque sensor at the output anvil 1622) although a more preferable slippage would be about 10 inch-pounds.

In some implementations, the bypass shaft 1610 may be operably coupled to the rotating mass 1604 via the magnetic slip clutch 1608. The bypass shaft 1610 may pass through a center of the electronic clutch 1612 and may engage a pinion in the drive path juncture 1620. During normal operation, the bypass shaft 1610 may engage the drive path juncture 1620, which causes the output anvil 1622 to rotate.

In some implementations, if the output anvil 1622 encounters a high torque load (e.g., which causes excessive reactionary torque being transmitted to the operator of the rotary tool 1600), then the magnetic slip clutch 1608 may slip (e.g., or begin to slip), which limits the reactionary torque that is transmitted to the operator of the rotary tool 1600. In other words, the magnetic slip clutch 1608 may decouple the bypass shaft 1610 and the output anvil from the rotating mass 1604 (e.g., based on slipping). In some implementations, the magnetic slip clutch 1608 may slip based on a slip torque of 2 to 50 inch-pounds.

In this way, the reactionary torque transmitted to the operator of the rotary tool 1600 may be limited. In some implementations, if the slip torque is exceeded, then the magnetic slip clutch 1608 slips, which causes a rotational speed associated with the output anvil 1622 to be reduced, temporarily. In other words, when the magnetic slip clutch 1608 slips, the output anvil 1622 slows down or stops based on the output anvil torque exceeding the slip torque.

In some implementations, a rotational speed sensor 1614 is a Hall Effect sensor and may be used to monitor the rotational speed of the output anvil 1622. The Hall Effect sensor may send, and a controller (e.g., a control board and/or a control circuit, among other examples) associated with the rotary tool 1600 may receive, an indication of the rotational speed of the output anvil 1622. Although the rotary tool 1600 is described as using the Hall effect sensor to monitor the rotational speed of the output anvil 1622, the rotary tool 1600 may use any suitable technique and/or sensor device to monitor the rotational speed of the output anvil 1622.

In some implementations, the controller may control an electronic clutch 1612, as described in more detail elsewhere herein. Accordingly, the controller may include various semiconductor components including but not limited to transistors, integrated circuits, and passive components such as inductors, capacitors etc.

In some implementations, the controller may cause the electronic clutch 1612 to be engaged. Engaging the electronic clutch 1612 causes the rotating mass 1604 to be operatively coupled to the output anvil 1622, as described in more detail elsewhere herein. Accordingly, for example, engaging the electronic clutch 1612 may increase a torque (e.g., may "boost" the torque) by coupling the rotational inertia of the rotating mass to the output anvil.

In some implementations, a frequency and/or duty cycle of the electronic clutch 1612 can be optimized to provide the optimized operating characteristics associated with the rotary tool 1600 (e.g., which may be based on operator preferences, operations, and/or other techniques, among other examples). As an example, the electronic clutch 1612 may be engaged at variable frequencies ranging from a single engagement up to 80 Hz.

In some implementations, the rotary tool 1600 may include only a single drive path (e.g., the rotary tool 1600 may not include the bypass shaft 1606). The frequency and/or duty cycle of the electronically activated clutch 1612 may be modulated based on an output rpm sensor, based on a fixed rate, or a rate dependent on how the trigger is depressed (e.g., a variable rate).

In some implementations, the secondary drive path may be associated with engaging the electronic clutch 1612. As an example, if the controller determines that the rotational speed of the output anvil 1622 has dropped below the desired design speed (e.g., when the magnetic slip clutch 1608 slips or begins slipping), then the controller may selectively activate the electronic clutch 1612, which causes the rotating mass to be operatively coupled to the output anvil 1622. Accordingly, a high rotational energy of the rotating mass 1604 may be transmitted to the output anvil 1622 to increase the output torque of the output anvil 1622. In other words, the motor 1624 drives the rotating mass 1604, which is then selectively coupled to and decoupled from the output anvil 1622 by the electronically activated clutch 1612. By selectively coupling the rotating mass, the torque at the output anvil is increased by at least 30%.

In some implementations, a one-way overrun bearing (e.g., the bypass shaft overrun bearing 1810 shown and described in connection with FIG. 3 and/or as described in more detail elsewhere herein) may be installed between the bypass shaft 1610 and a center drive (e.g., the center drive 1804 shown and described in connection with FIG. 3 and/or as described in more detail elsewhere herein) to reduce reactionary torque (e.g., internal reactionary torque) and potential associated wear of one or more components of the rotary tool 1600 (e.g., which is dependent on a construction of the clutch being used by the rotary tool 1600).

In some implementations, the activation of the electronic clutch 1612 may be associated with reducing the motor power and or speed by 10% or more such as to further decouple the reactionary torque communicated from the output anvil to the operator. In some implementations, the decoupling of the motor 1624 (e.g., by disengaging or reducing the power to the motor 1624) reduces a pass-through torque (e.g., torque coupled from the output anvil 1622 back through to the motor 1624, a motor mount, and a handpiece of the rotary tool 1600). Furthermore, a rotational energy associated with the rotating mass 1604 can access the rotating inertia of the motor 1624 with minimal to zero increase in reflected torque since the motor rotor inertia is uncoupled or minimally coupled to the tool (e.g., free spinning or coasting).

In some implementations, an amount of time that the rotating mass 1604 is engaged, via the electronic clutch 1612 (e.g., via activation of the electronic clutch 1612), may be between a range (e.g., between approximately 1 millisecond and 100 milliseconds or less than (or equal to) 50 milliseconds, among other examples). In some implementations, the rotating mass 1604 increases a peak output torque, as measured at the output anvil 1622, by (or at least by) 100% over a main drive axis (e.g., the first drive path through the bypass shaft 1610 as described in more detail elsewhere herein) for a period of at least 1 millisecond.

In some implementations, the electronic clutch 1612 engages (e.g., activates) in less than (or equal to) twenty milliseconds, where engagement of the electronic clutch 1612 is defined as moving from 10% to 80% of transmitted torque through the electronic clutch 1612. The electronic clutch 1612 may be disengaged (e.g., may be deactivated) to allow the motor 1624 to drive reaccelerate the rotating mass 1604.

In some implementations, if the controller determines that the output speed (e.g., of the output anvil 1622) is in the desired output rpm range, then the controller enables the rotary tool 1600 to function normally (e.g., the output anvil 1622 is driven by the bypass shaft 1610), and the electronic clutch 1612 is deactivated (e.g., which causes the rotating mass 1604 to be decoupled from the output anvil 1622). If the controller determines that the output speed (e.g., an output rotational speed of the output anvil 1622) drops below the design speed, which may be associated with a torque threshold, then the controller may activate and deactivate (e.g., in a pulsed manner) the electronic clutch 1612 to overcome the excessive load torque encountered by the output anvil 1622.

With reference to FIGS. 1-4, using the magnetic slip clutch 1608 and the one way bearing 1810 on the bypass shaft 1610 greatly reduces contact wear between components. An advantage of coupling the rotating mass 1604 through a 1:1 ratio on the drive path juncture 1620 is that there will be no reactionary torque transmitted to the housing through the drive path juncture 1620. It is understood that coupling the electronic clutch 1612 to a 1:1 gear ratio is the same as (or similar to) coupling the electronic clutch 1612 directly to the output anvil 1622. The one way bearing 1810 may reduce the wear which may occur in a contacting slip clutch such as a ball cup spring relief clutch or a friction clutch. It is noted that the magnetic slip clutch 1608 can be used independently of the one way bearing 1810 on the bypass shaft 1610 (e.g., the magnetic slip clutch 1608 may be used without the one-way bearing).

Figure 5A:
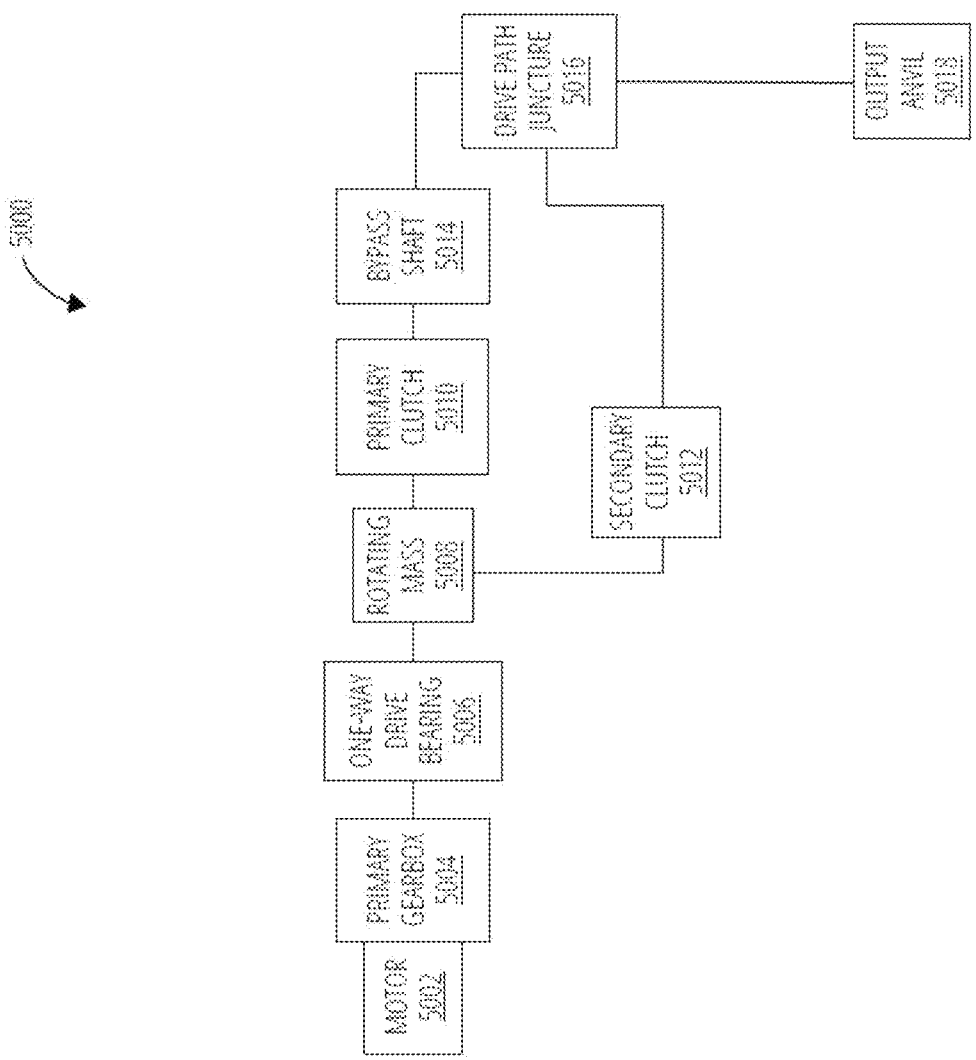
FIGS. 5A-5B are diagrams of example rotary tools.
Figure 5B:
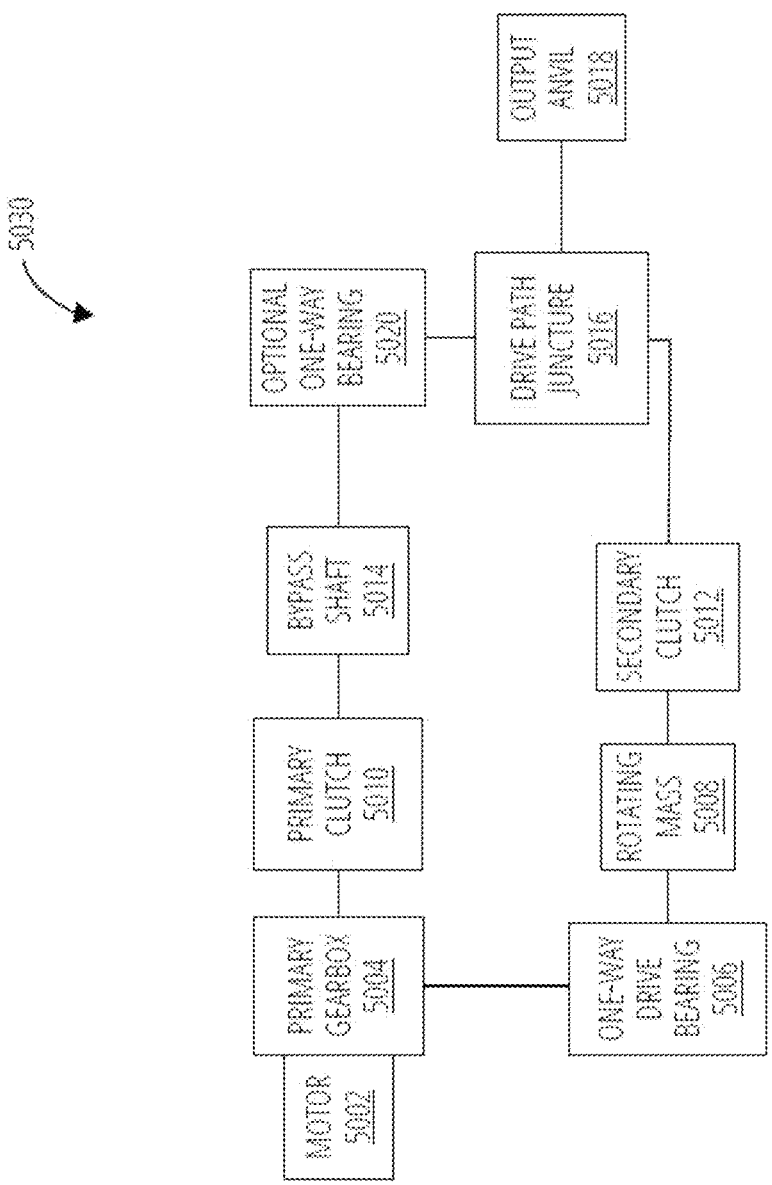

FIGS. 5A-5B are diagrams of example rotary tools 5000 and 5030 respectively. As shown in FIG. 5A, the rotary tool 5000 includes a motor 5002, a primary gearbox 5004, a one-way drive bearing 5006 (which can be optional), a rotating mass 5008, a primary clutch 5010, a secondary clutch 5012, a bypass shaft 5014, a drive path juncture 5016, and an output anvil 5018.

In a first drive path, the motor 5002 drives the output anvil 5018 via the primary gearbox 5004, the one-way drive bearing 5006, the rotating mass 5008, the primary clutch 5010, the bypass shaft 5014 and the drive path juncture 5016. In a second drive path, the motor 5002 drives the output anvil 5018 via the primary gearbox 5004, the one-way drive bearing 5006, the rotating mass 5008, the secondary clutch 5012, and the drive path juncture 5016. Accordingly, for example, the rotary tool 5000 of FIG. 5A may cause, via the first drive path, the output anvil 5018 to rotate at a speed and may cause, by selectively enabling the second drive path, the rotating mass 5008 to engage to (e.g., through the secondary clutch 5012 and the drive path juncture 5016) the output anvil 5018 to increase the torque to the output anvil 5018.

As shown in FIG. 5B, the rotary tool 5030 includes a motor 5002, a primary gearbox 5004, a one-way drive bearing 5006 (which can be optional), a rotating mass 5008, a primary clutch 5010, a secondary clutch 5012, a bypass shaft 5014, a drive path juncture 5016, an output anvil 5018, and an optional one-way bearing 5020 (e.g., positioned between the bypass shaft 5014 and the drive path juncture 5016). The motor 5002 of the rotary tool 5030 of FIG. 5B drives the rotating mass 5008 and the secondary clutch 5012 independently.

In a first drive path, the motor 5002 drives the output anvil 5018 via the primary gearbox 5004, the primary clutch 5010, the bypass shaft 5014, the optional one-way bearing 5020, and the drive path juncture 5016. In a second drive path, the motor 5002 drives the output anvil 5018 via the primary gearbox 5004, the one-way drive bearing 5006, the rotating mass 5008, the secondary clutch 5012, and the drive path juncture 5016. Accordingly, for example, the rotary tool 5030 of FIG. 5B may cause, via the first drive path, the output anvil 5018 to rotate at a speed and may cause, by selectively enabling the second drive path, the rotating mass 5008 to engage to (e.g., through the secondary clutch 5012 and the drive path juncture 5016) the output anvil 5018 to increase the torque to the output anvil 5018.

Figure 6A:
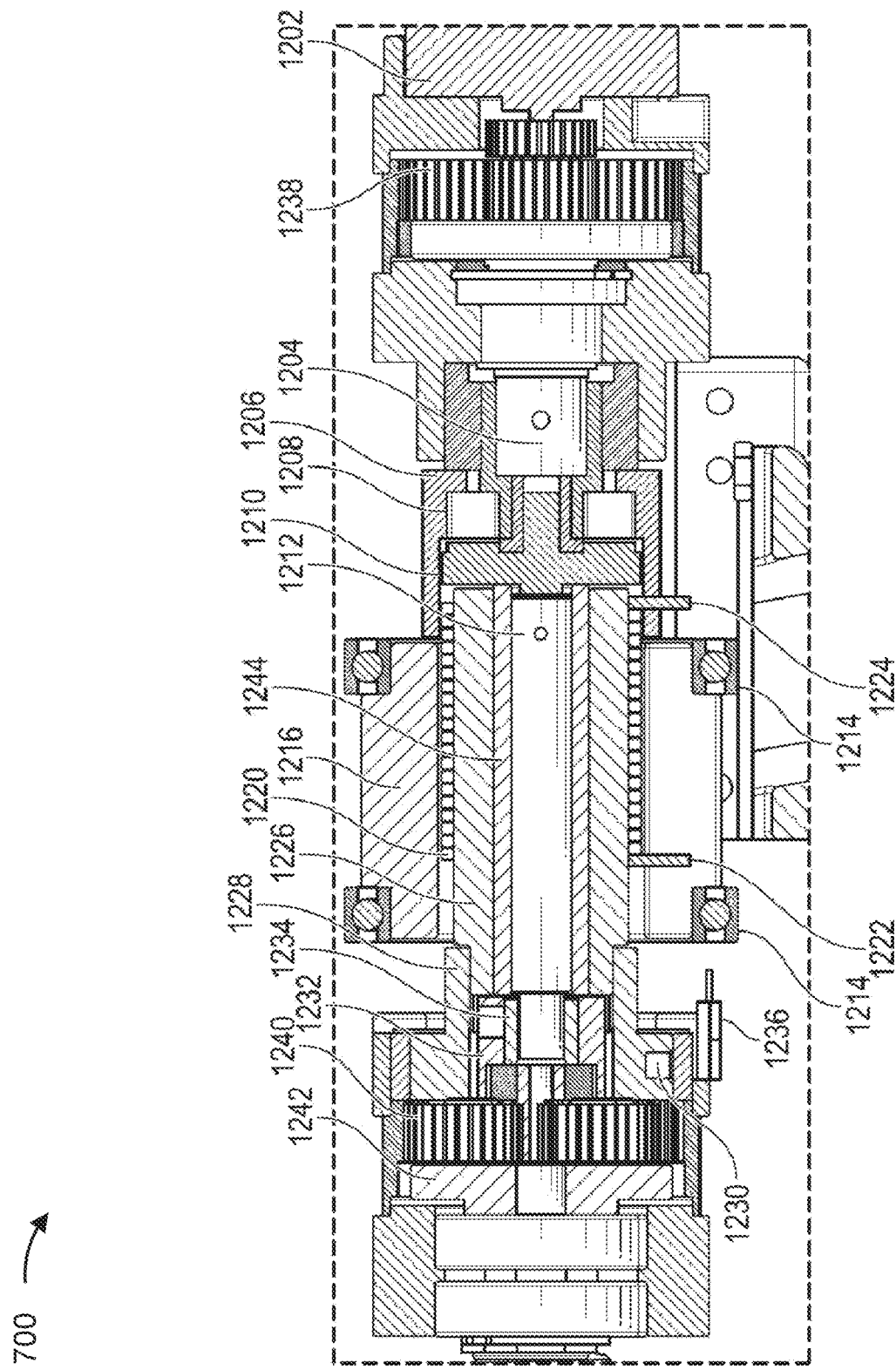
FIGS. 6A-6G are diagrams of example rotary tools.
Figure 6B:
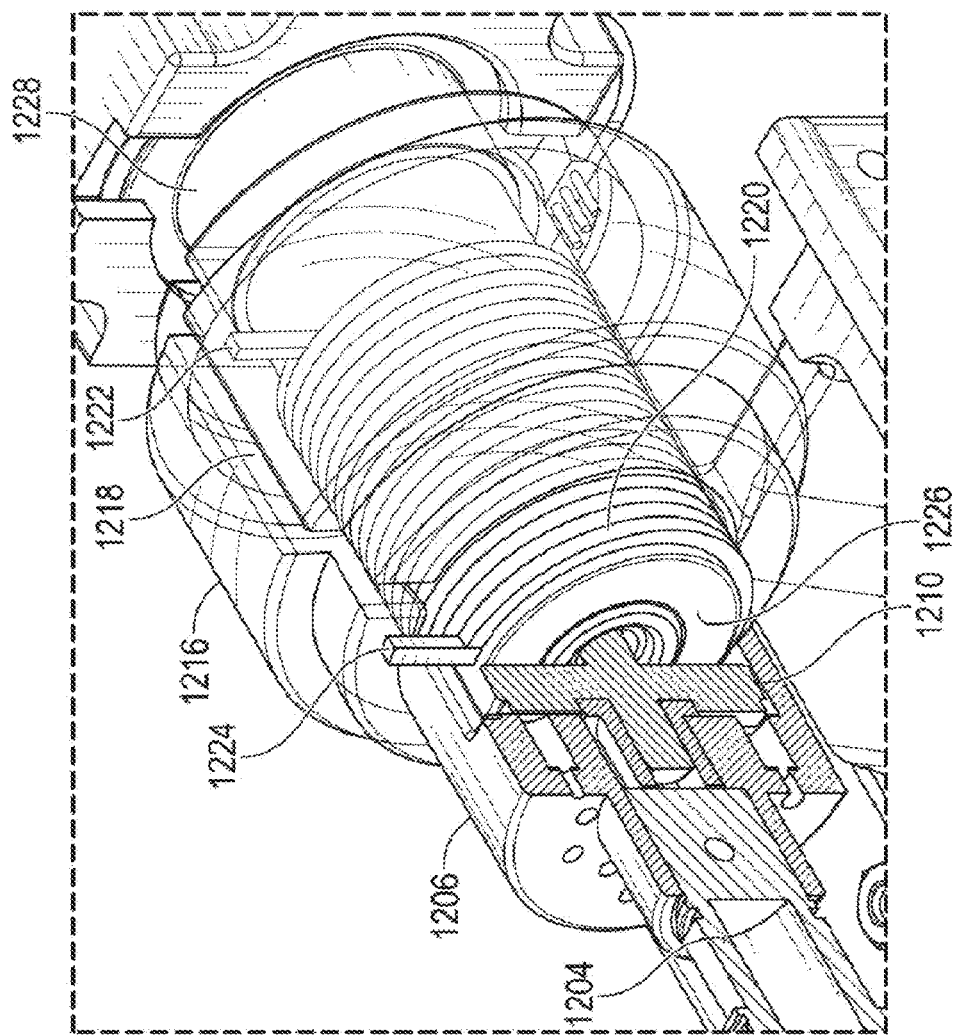
Figure 6C:
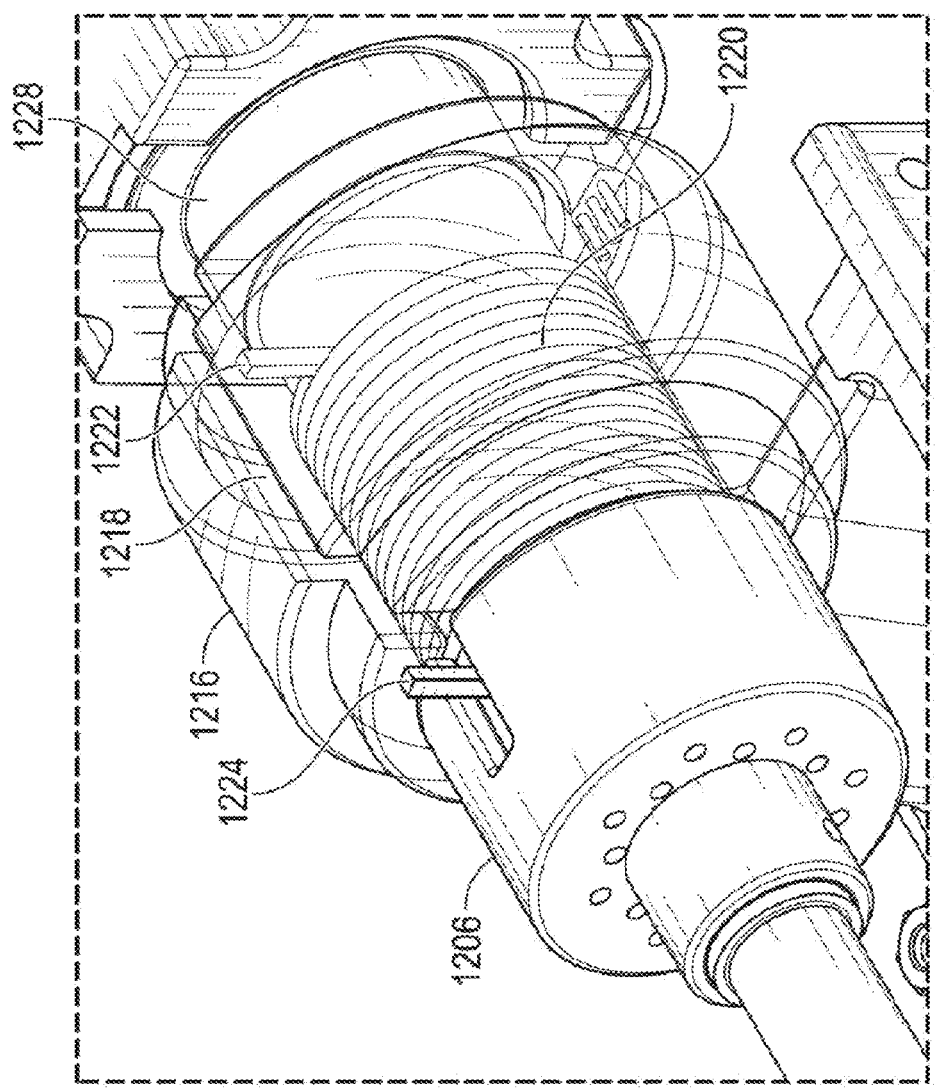

FIG. 6A is a diagram of an example rotary tool 1200. FIGS. 6B-6C are partial diagrams of the rotary tool 1200 of FIG. 6A. As shown in FIGS. 6A-6C, the rotary tool 1200 includes a motor 1202, a drive shaft 1204, a clutch driver 1206 (e.g., a spring-trip slip-clutch driver (STSCD)), one or more magnets 1208 (e.g., one or more STSCD magnets), a bypass drive 1210, a bypass shaft 1212, ball bearings 1214, a flywheel 1216, a flywheel slot 1218, a wrap spring 1220, a flywheel spring tang 1222, a control spring tang 1224, a wrap down hub 1226, a carriage plate driver 1228, carriage plate driver magnets 1230, a bypass pinion 1232, a one-way bearing 1234, an rpm sensor 1236, a primary gearbox 1238, drive path juncture 1240, an output anvil 1242, and a bypass sleeve bushing 1244 (e.g., that enables relative motion between the bypass shaft 1212 and the wrap down hub 1226).

In some implementations, the rotary tool 1200 may cause the output anvil 1242 to rotate using at least one of a first mode (e.g., associated with a first pathway) or a second mode (e.g., associated with a second pathway), as described in more detail elsewhere herein. As an example, when operating in the first mode, the rotary tool 1200 may use the bypass drive 1210 to cause the output anvil 1242 to rotate. As another example, when operating in the second mode, the rotary tool may use the flywheel 1216 to cause the output anvil 1242 to rotate.

In some implementations, an operator of the rotary tool 1200 may cause the motor 1202 to rotate (e.g., by interacting with an operator interface of the rotary tool 1200). The motor 1202 drives the draft shaft 1204, which, in turn, drives the clutch driver 1206 (e.g., the STSCD driver). When the rotary tool 1200 operates in the first mode, the clutch driver 1206 drives the bypass drive 1210 through a slip clutch (e.g., a magnetic slip clutch). For example, the clutch driver 1206 may use the one or more magnets 1208 to drive the bypass drive 1210, which, in turn, drives the bypass shaft 1212. The bypass shaft 1212 is operatively coupled to the bypass pinion 1232. The bypass drive 1210 and the bypass shaft 1212 may drive the bypass pinion 1232 through the one-way bearing 1234. The bypass pinion 1232 drives the output anvil 1242 through the drive path juncture 1240.

In some implementations, when a load torque on the output anvil 1242 is higher than a slip torque (e.g., a slip torque associated with the clutch driver 1206, the one or more magnets 1208, and the bypass drive 1210), the bypass drive 1210 and the bypass shaft 1212 slip. This causes a rotational speed of the carriage plate driver 1228 to be reduced (e.g., the carriage plate driver 1228 will slow down or stop moving).

In some implementations, the carriage plate driver magnets 1230 may be disposed on the carriage plate driver 1228 (e.g., the carriage plate driver magnets 1230 may be regularly spaced on the carriage plate driver 1228). The rpm sensor 1236 may be positioned to detect movement of the carriage plate magnets 1230. The rpm sensor 1236 may detect a rotational speed of the carriage plate driver 1228 based on the movement of the carriage plate driver magnets 1230. The rpm sensor 1236 may send, and a controller (e.g., associated with a control board) may receive, an indication of the rotational speed of the carriage plate driver 1228. The controller may activate, based on determining that the rotational speed of the carriage plate driver 1228 satisfies (e.g., has dropped below) a rotational speed threshold, the second mode (e.g., the controller may cause the rotary tool 1200 to operate in the second mode by engaging the flywheel 1216).

As an example, the rotary tool 1200 may drive the clutch driver 1206 which, in turn, drives the wrap spring 1220 through the flywheel spring tang 1222 and the control spring tang 1224. The flywheel spring tang 1222 may be aligned within the flywheel slot 1218 and the control spring tang 1224 may be aligned within a slot of the clutch driver 1206. As the clutch driver 1206 drives the control spring tang 1224 in a first direction, the control spring tang 1224 generates a radial force that unwinds coils of the wrap spring 1220 (e.g., the wrap spring 1220 expands). In other words, the control spring tang 1224 may cause the wrap spring 1220 to partially unwind when the control spring tang 1224 is driven in the first direction. In this way, because the wrap spring 1220 unwinds when the rotary tool 1200 operates in the first mode (e.g., using the bypass drive 1210 and the bypass shaft 1212 to rotate the control spring tang 1224 in the first direction), the wrap spring 1220 does not interact with the wrap down hub 1226 during operation of the rotary tool 1200 in the first mode.

Additionally, as the clutch driver 1206 drives the control spring tang 1224 in the first direction, the control spring tang 1224 causes the flywheel 1216 to rotate (e.g., accelerate) in the first direction, which enables the flywheel 1216 to generate and store rotational kinetic energy In some implementations, the controller may activate the second mode (e.g., the controller may cause the rotary tool 1200 to operate in the second mode by engaging the flywheel 1216) based on determining that the bypass drive 1210 is slipping and the controller may cause the rotary tool 1200 to operate in the second mode to overcome the excessive load torque.

In some implementations, to operate in the second mode, the controller may reduce a rotational speed of the clutch driver 1206 (e.g., by causing a rotational speed of the motor 1202 to be reduced), which causes a rotational speed of the control spring tang 1224 to be reduced. In response to the rotational speed of the control spring tang 1224 being reduced, the flywheel 1216 will continue to rotate due to its high rotational inertia. The flywheel 1216 drives the flywheel spring tang 1222, and the flywheel spring tang 1222 winds the coils of the wrap spring 1220 (e.g., the wrap spring 1220 contracts) to operatively couple the wrap spring 1220 to the wrap down hub 1226. In other words, the flywheel spring tang 1222 may cause the wrap spring 1220 to operatively couple to the wrap down hub 1226. This results in the flywheel 1216 being operatively coupled to the output anvil 1242 (e.g., via the wrap spring 1220 and the wrap down hub 1226). In this way, when operating in the second mode, the flywheel 1216 applies a high rotary energy pulse to the output anvil 1242 to overcome the excessive torque load. After the high energy pulse has been applied to the output anvil 1242, the controller can increase the rotational speed of the motor 1202 which releases the wrap spring 1220 from the wrap down hub 1226 and accelerates the flywheel 1216 (e.g., associated with the first mode of operation). The rpm sensor 1236 indicates to the controller when to shift between first mode and second mode continuously throughout the operational cycle of the tool.

Figure 6D:
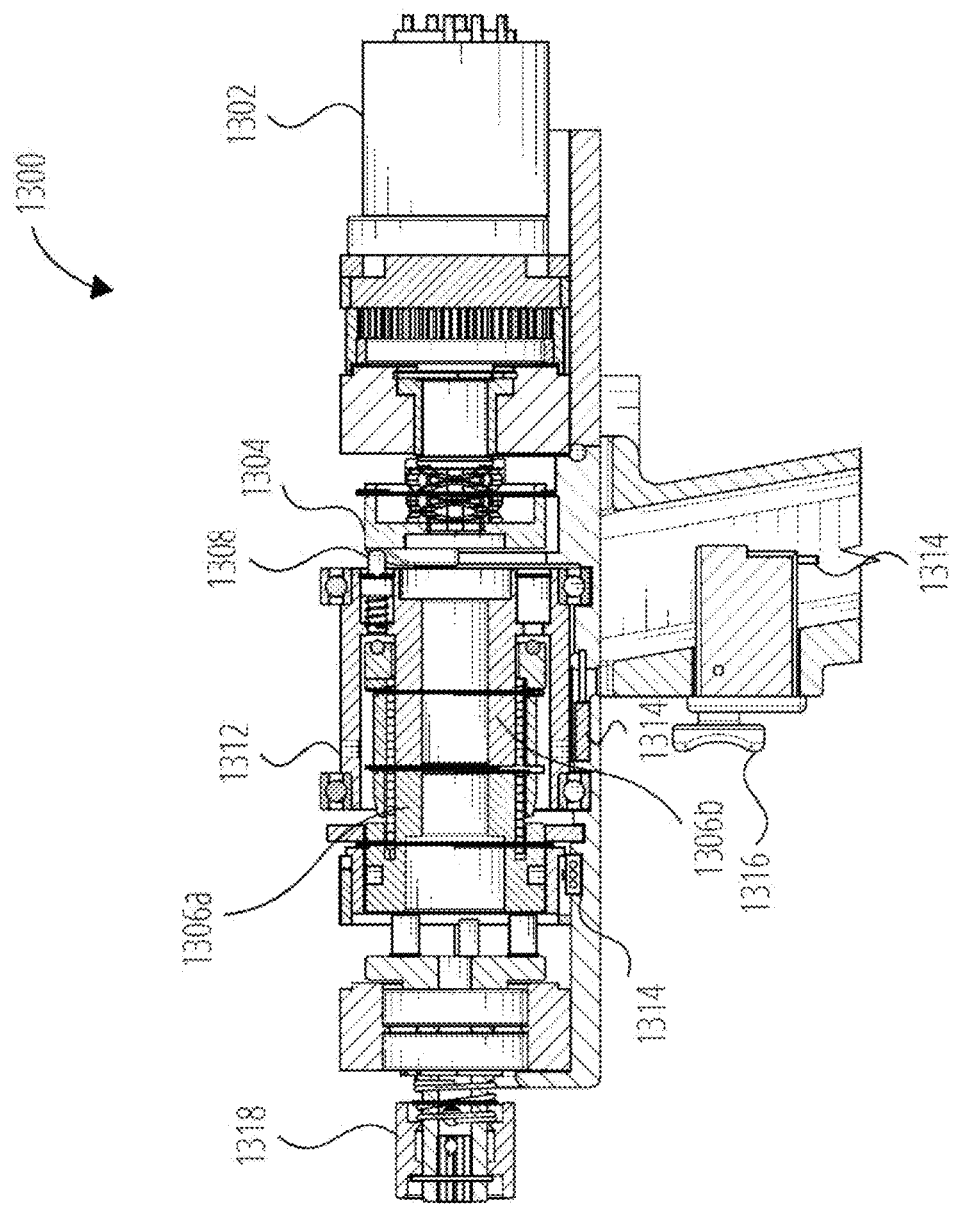
Figure 6E:
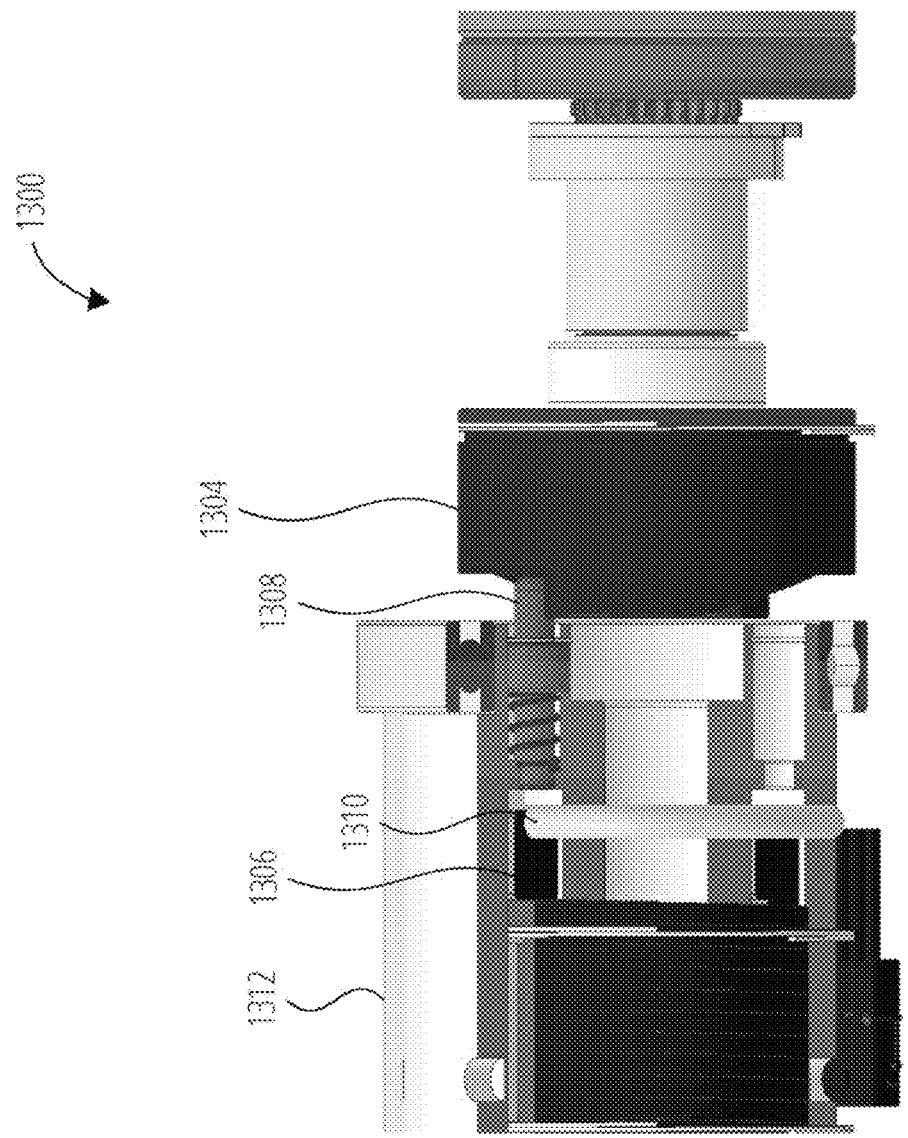
Figure 6F:
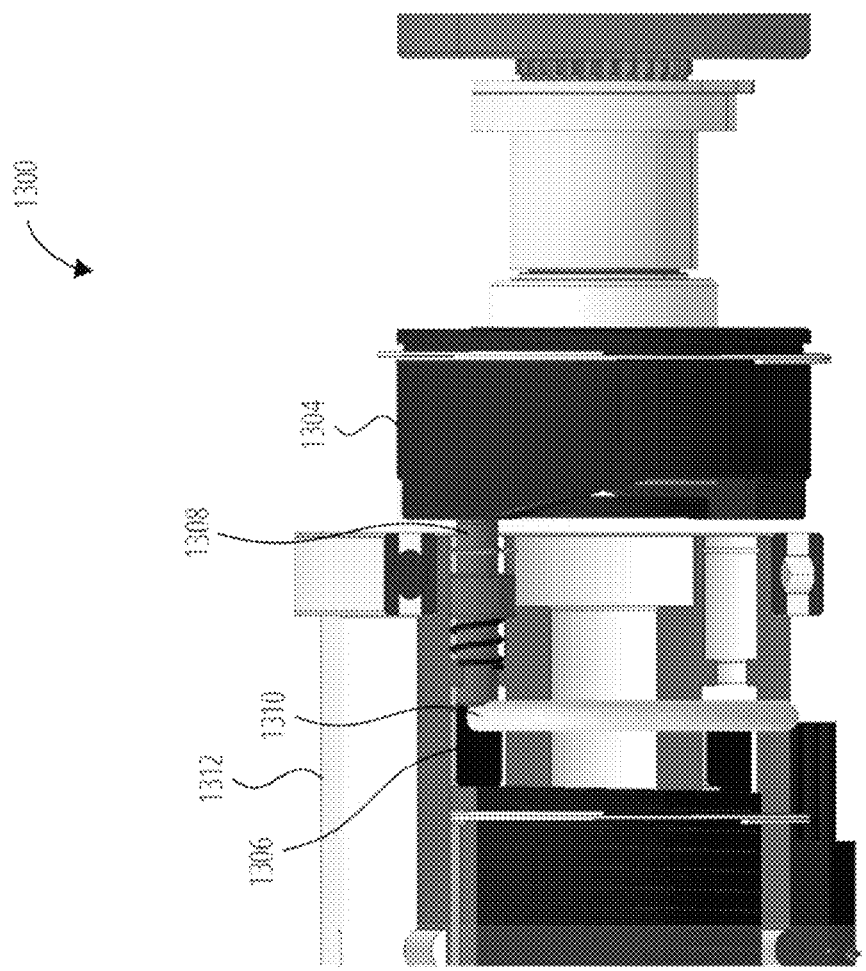

FIGS. 6D-F are diagrams of an example rotary tool 1300. The rotary tool 1300 of FIG. 6D includes a motor 1302, a drive shaft cam 1304, a clutch 1306, a carrier driver wrap down hub 1306a, a flywheel wrap down hub 1306b, spring actuators 1308, a clutch actuator ring 1310, a flywheel 1312, one or more sensors 1314 (e.g., one or more rpm sensors, among other examples), a trigger mechanism 1316, and an output anvil 1318. In some implementations, the motor 1302 drives (e.g., by modulating, via a controller, a motor speed or in response to displacement of the trigger mechanism 1316) the drive shaft cam 1304, which, in turn, rotates the flywheel 1312 by pushing on the spring actuators 1308, as described in more detail elsewhere herein.

The flywheel 1312 stores rotational kinetic energy (e.g., in a same or similar manner as described in more detail elsewhere herein). Once the flywheel 1312 has been accelerated to a percentage of a maximum rpm of the flywheel 1312 (e.g., at least 80% of the maximum rpm of the flywheel 1312), a controller can reduce the power applied to the motor 1302 which causes a speed of the drive shaft cam 1304 to decrease relative to the rotational speed of the flywheel 1312. The flywheel 1312 will over-rotate and ramps on the drive shaft cam 1304 force the spring actuators 1308 forward into the clutch actuator ring 1310 (as shown in FIGS. 6E-6F). This actuates the clutch 1306 (e.g., this actuates a wrap spring clutch by applying a torque to a wrap spring tang causing it to wrap down and couple the flywheel wrap-down hub 1306b to the carrier driver wrap-down hub 1306a). This increases the rotational speed and applies a high output torque to the output anvil 1318. It is understood that the carrier driver wrap-down hub 1306a and the output anvil 1318 can be combined into a single part. After the high output torque is applied to the output anvil 1318 (e.g., after the clutch is engaged), the spring actuators 1308 will disengage from the ramps of the drive shaft cam 1304 and the controller will increase power to the motor 1302 to reaccelerate the flywheel 1312. In some implementations, the clutch 1306 can be engaged for a period of time between 1 and 100 ms. The cycle above can be repeated at between 1 to 80 Hz.

Based on one or more parameters and/or conditions (e.g., one or more duty cycles, frequencies, speeds of the output anvil 1318, time intervals, and/or displacements of the trigger mechanism 1316, among other examples), the motor 1302 accelerates which causes the flywheel 1312 to reaccelerate. Based on the flywheel 1312 reaccelerating, the clutch 1306 disengages from the output anvil 1318.

Figure 6G:
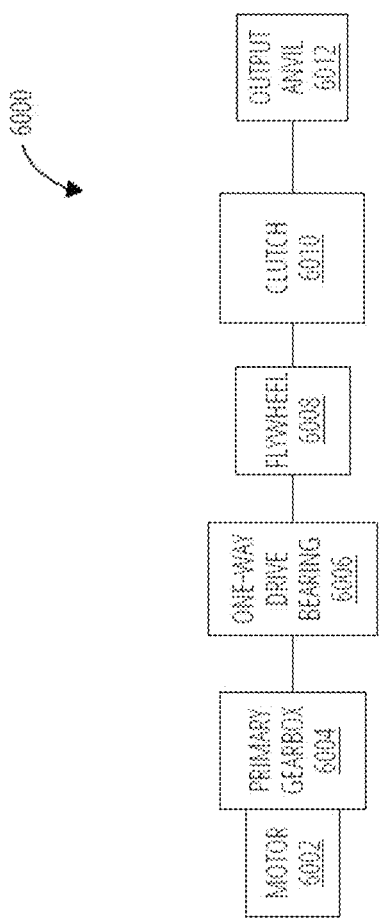

FIG. 6G is a diagram of an example rotary tool 6000. As shown in FIG. 6G, the rotary tool 6000 includes a motor 6002, a primary gearbox 6004, a one-way drive bearing 6006 (which can be optional), a flywheel 6008, a clutch 6010, and an output anvil 6012. The motor 6002 drives the output anvil 6012 via the primary gearbox 6004, the one-way drive bearing 6006, the flywheel 6008, and the clutch 6010 (e.g., in a same or similar manner as described in more detail elsewhere herein).

As indicated above, FIGS. 1-6G are provided as examples. Other examples may differ from what is described with regard to FIGS. 1-6G. The number and arrangement of the various components shown in FIGS. 1-6G are provided as examples. In practice, there may be additional components, fewer components, different components, or differently arranged components than those shown in FIGS. 1-6G. Additionally, or alternatively, a set of components (e.g., one or more components) shown in FIGS. 1-6G may perform one or more functions described as being performed by another set of components shown in FIGS. 1-6G.

Figure 7:
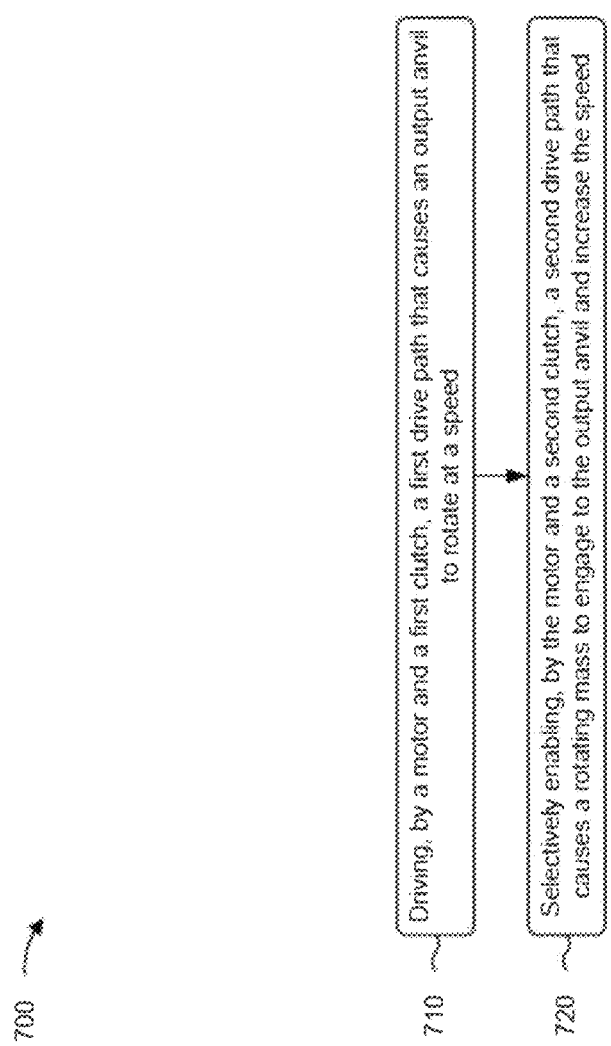
FIG. 7 is a flowchart of an example process associated with operating a rotary tool, in accordance with some embodiments of the present disclosure.

FIG. 7 is a flowchart of an example process 700 associated with operating a rotary tool. As shown in FIG. 7, process 700 may include driving, by a motor and a first clutch, a first drive path that causes an output anvil to rotate at a speed (block 710). As an example, process 700 may include driving, by the motor and the first clutch, the first drive path that causes the output anvil to rotate at the speed, as described in more detail elsewhere herein. As further shown in FIG. 7, process 700 may include selectively enabling, by the motor and a second clutch, a second drive path that causes a rotating mass to engage the output anvil and increase the speed (block 720). As an example, process 700 may include selectively enabling, by the motor and the second clutch, the second drive path that causes the rotating mass to engage the output anvil and increase the speed, as described in more detail elsewhere herein.

In some implementations, the second drive path may be selectively enabled when the speed of the output anvil drops to less than a percentage of a design speed (e.g., less than 99% of the design speed). In some implementations, the first clutch may be a slip clutch and the second drive path may be selectively enabled when the slip clutch begins slipping. In some implementations, the second drive path may be selectively enabled based on at least one of a duty cycle or a frequency. In some implementations, selectively enabling the second drive path may causes an output torque at the output anvil to increase by at least 30%. In some implementations, the engagement of the rotating mass to the output anvil may counteract a load torque received at the output anvil. In some implementations, the load torque may be at least one of approximately 2 to 50 inch-pounds.

Although FIG. 7 shows example blocks of process 700, in some implementations, process 700 may include additional blocks, fewer blocks, different blocks, or differently arranged blocks than those depicted in FIG. 7. Additionally, or alternatively, two or more of the blocks of process 700 may be performed in parallel. The process 700 is an example of one process that may be performed by one or more devices described herein. These one or more devices may perform one or more other processes based on operations described herein, such as the operations described in connection with FIGS. 1-7. Moreover, while the process 700 has been described in relation to the devices and components of the preceding figures, the process 700 can be performed using alternative, additional, or fewer devices and/or components. Thus, the process 700 is not limited to being performed with the example devices, components, hardware, and software explicitly enumerated in the preceding figures.

As used herein, the term "component" is intended to be broadly construed as hardware, firmware, or a combination of hardware and software. It will be apparent that systems and/or methods described herein may be implemented in different forms of hardware, firmware, and/or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be used to implement the systems and/or methods based on the description herein.

As used herein, satisfying a threshold may, depending on the context, refer to a value being greater than the threshold, greater than or equal to the threshold, less than the threshold, less than or equal to the threshold, equal to the threshold, not equal to the threshold, or the like.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set. As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiple of the same item.

No element, act, or instruction used herein should be construed as critical or essential unless explicitly described as such. Also, as used herein, the articles "a" and "an" are intended to include one or more items and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, or a combination of related and unrelated items), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

In the preceding specification, various example embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

What is claimed is:

1. A rotary tool, comprising:
   a motor;
   a drive shaft operatively coupled to the motor;
   an output anvil;
   a rotating mass;
   at least one electronically activated clutch
      wherein the at least one clutch is operatively coupled to the rotating mass and the output anvil,
      wherein the clutch engages the rotating mass to the output anvil for a period of time, and
      wherein after such engagement the clutch disengages the rotating mass from the output anvil to allow the rotating mass to reaccelerate; and
   a controller configured to:
      cause the clutch to selectively couple the rotating mass to the output anvil at a frequency of at least five hertz for part of an operation.

2. The rotary tool of claim 1, further comprising:
   a controller configured to:
      cause the clutch to selectively engage and disengage the rotating mass to the output anvil based on at least one of:
         a duty cycle,
         a frequency, or
         a deviation in a speed of the output anvil from a design speed.

3. The rotary tool of claim 1, wherein at least one clutch engages with a wrap spring.

4. The rotary tool of claim 1, further comprising:
   a controller configured to:
      deactivate the motor for at least a portion of a time during which the clutch is coupling the rotating mass to the output anvil.

5. The rotary tool of claim 1, further comprising:
   a one-way drive bearing operatively coupled to the rotating mass,
   wherein the motor drives the rotating mass via the one-way drive bearing to generate rotational kinetic energy that is stored by the rotating mass.

6. The rotary tool of claim 1, further comprising:
   a second clutch that couples the motor, the drive shaft, and the output anvil,
   wherein the second clutch is at least one of:
      a slip-clutch, or
      a break-away clutch.

7. A method for operating a rotary tool, the rotary tool including a motor, a first clutch, a first drive path, a second drive path, a second clutch, a rotating mass, and an output anvil, the method comprising:
   driving, by the motor and the first clutch, a first drive path that causes the output anvil to rotate at a speed; and
   selectively enabling, by the motor and the second clutch, a second drive path that causes the rotating mass to engage to the output anvil and increase a torque delivered to the output anvil.

8. The method of claim 7, wherein the second drive path is selectively enabled when the speed of the output anvil deviates from a design speed.

9. The method of claim 7, wherein the first clutch is a slip clutch, and
   wherein the second drive path is selectively enabled when the slip clutch begins slipping.

10. The method of claim 9, wherein the slip clutch begins slipping at between 1 inch-pound and 25 inch-pounds.

11. The method of claim 7, wherein the second drive path is selectively enabled based on at least one of:
    a duty cycle, or
    a frequency.

12. The method of claim 7, wherein selectively enabling the second drive path causes the torque delivered to the output anvil to increase by at least 30%.

13. A rotary tool, comprising:
    a motor;
    a controller;
    a drive shaft operatively coupled to the motor;
    an output anvil;
    a flywheel; and
    at least one clutch,
       wherein the at least one clutch is operatively coupled to the flywheel and the output anvil,
       wherein the at least one clutch engages the flywheel to the output anvil by modulating, via the controller, a motor speed,
       wherein after the at least one clutch has been engaged for a period of time, the at least one clutch disengages the flywheel from the output anvil and the motor reaccelerates the flywheel, and
       wherein the flywheel reaches at least 80% of a maximum rotational speed of the flywheel before the at least one clutch engages the flywheel to the output anvil.

14. The rotary tool of claim 13, wherein the controller is configured to activate the clutch based on at least one of:
    a duty cycle,
    a frequency, or a deviation in a speed of the output anvil from a design speed.

15. The rotary tool of claim 13, further comprising:
a one-way bearing that operatively couples the motor to the flywheel.

16. The rotary tool of claim 13, wherein the controller is configured to deactivate the motor based on causing the at least one clutch to selectively couple the flywheel to the output anvil.

17. The rotary tool of claim 13, wherein selectively coupling the flywheel to the output anvil causes an increase in a torque of the output anvil of at least 30%.

18. The rotary tool of claim 13, wherein the at least one clutch engages with a wrap spring.

* * * * *